United States Patent
Rost et al.

(10) Patent No.: US 12,409,433 B2
(45) Date of Patent: Sep. 9, 2025

(54) MICROCAPSULES

(71) Applicant: SYMRISE AG, Holzminden (DE)

(72) Inventors: Benjamin Rost, Bodenwerder (DE);
Ralf Bertram, Holzminden (DE);
Daniela Gregor, Holzminden (DE);
Lara-Joy Kleine-Benne, Holzminden (DE)

(73) Assignee: Symrise AG, Holzminden (DE)

( * ) Notice: Subject to any disclaimer, the term of this patent is extended or adjusted under 35 U.S.C. 154(b) by 1134 days.

(21) Appl. No.: 17/297,712

(22) PCT Filed: Dec. 2, 2019

(86) PCT No.: PCT/EP2019/083330
§ 371 (c)(1),
(2) Date: May 27, 2021

(87) PCT Pub. No.: WO2020/114975
PCT Pub. Date: Jun. 11, 2020

(65) Prior Publication Data
US 2022/0040659 A1    Feb. 10, 2022

(30) Foreign Application Priority Data
Dec. 3, 2018 (WO) .................. PCT/EP2018/083315

(51) Int. Cl.
| | |
|---|---|
| *B01J 13/22* | (2006.01) |
| *A61K 8/11* | (2006.01) |
| *A61Q 13/00* | (2006.01) |
| *B01J 13/14* | (2006.01) |
| *B01J 13/20* | (2006.01) |
| *C11D 3/50* | (2006.01) |
| *C11D 17/00* | (2006.01) |

(52) U.S. Cl.
CPC .................. *B01J 13/22* (2013.01); *A61K 8/11* (2013.01); *A61Q 13/00* (2013.01); *B01J 13/14* (2013.01); *B01J 13/206* (2013.01); *C11D 3/505* (2013.01); *C11D 17/0039* (2013.01); *A61K 2800/56* (2013.01)

(58) Field of Classification Search
None
See application file for complete search history.

(56) References Cited

FOREIGN PATENT DOCUMENTS

| | | | |
|---|---|---|---|
| CN | 102438740 A | * 5/2012 | ............. A01N 25/28 |
| DE | 1 817 316 A1 | 12/1969 | |
| DE | 10 2017 111445 A1 | 11/2018 | |
| GB | 1 257 178 A | 12/1971 | |
| WO | 2017/001672 A1 | 1/2017 | |

OTHER PUBLICATIONS

CN 102438740 A Eng translation (Year: 2012).*

* cited by examiner

*Primary Examiner* — Jeffrey D Washville
(74) *Attorney, Agent, or Firm* — Dilworth & Barrese, LLP

(57) ABSTRACT

What are proposed are microcapsules comprising
(a) a core comprising at least one active, and
(b) a capsule wall,
wherein the capsule wall consists of at least three polymer layers and at least one of the polymer layers consists of a first phenolic resin, wherein the first phenolic resin comprises 3% to 50% by weight of moieties that derive from at least one aromatic polyol, and at least one further polymer layer consists of a second phenolic resin, wherein the second phenolic resin comprises 3% to 50% by weight of moieties that derive from at least one triphenol.

20 Claims, 2 Drawing Sheets

MICROCAPSULES

FIELD OF THE INVENTION

The invention is in the field of microcapsules and the use thereof in cosmetic formulations, pharmaceutical products, domestic and cleaning products and industrial compositions, for example adhesive and coating compositions, paints, varnishes, binders, materials such as plastics, paper, textiles, lubricants, building materials, dyes, organic and inorganic powders, pigment dispersions, agrochemicals, phase transition materials, flame retardants, and of the production of the capsules.

BACKGROUND OF THE INVENTION

For a multitude of applications, from pharmacy through cosmetics and washing and cleaning compositions up to fertilizers, the delayed release of actives from a capsule shell has become increasingly important in recent years. It is also desirable in many cases in the foods sector when flavorings in particular are released not spontaneously but in a time-delayed manner on introduction into water or chewing ("controlled release").

It is thus well known that constituents such as fragrances, insecticides, anti-odor substances, fungicides and mildewicides and the like can be encapsulated in a microcapsule comprising a solid shell or membrane that protects them from their immediate environment. A popular method of producing such encapsulated formulations is to disperse the constituent in a liquid and to produce a polymer membrane on the surface of the droplets. Examples of suitable methods include simple and complex coacervation of gelatin with gum arabic, followed by crosslinking with glutaraldehyde. It is possible in principle to use many polymers or polymer mixtures capable of forming insoluble complexes underspecific conditions in order to form such interfacial membranes by what is called a polymer phase separation method.

The most important microcapsules include those of the amino resin type. These capsules are produced in a simplified manner in that an O/W emulsion comprising the water-soluble monomer, what is called an amine-formaldehyde precondensate, and the water-insoluble active, for instance a perfume oil, is first produced under high shear and in the presence of emulsifiers. The polycondensation is initiated by a change in pH, for example by setting the pH to about 3.5 by addition of acid. The polycondensates are deposited on the oil droplets in the emulsion and gradually encase them. On conclusion of the polycondensation, a microcapsule dispersion has formed from the emulsion. However, the capsules still have a soft elastic shell that still does not give the necessary diffusion stability and texture properties. There is therefore a subsequent third step in which the temperature is raised to about 60° C., which leads to crosslinking of the polymers in the wall and to curing of the capsules. A corresponding method is known, for example, from EP 2111214 B1 (GIVAUDAN).

A problem here, however, is that the above-described capsules are so stable that the encapsulated active, for example perfume oil, is not released in time to obtain a satisfactory result. It is thus necessary to use additional free unencapsulated perfume oil, which causes additional work and costs, since this perfume oil is different than the encapsulated perfume oil with regard to various properties such as intensity and quality.

A further strategy is the "scratch-and-sniff" system. If these microcapsules are applied to fragrances, they are typically used to generate surprising sensory effects, such as elevated perfume intensity or an impact, at a time when the microcapsules are rubbed by the action of pressure or friction. However, a disadvantage of this system is that the capsules generally suffer from serious stability problems, such as the extraction of the perfume through the conjugated effect of the surfactants, especially after prolonged storage at elevated temperatures. This leads to a loss of perfume. One way of getting round this is to strengthen the wall of the microcapsules by various means, for example by increasing the crosslinking density of the wall or applying a coating thereto. However, this generally leads to an increase in the stress required to break the microcapsules and consequently makes it more difficult to release the encapsulated fragrance.

It is thus an object of the invention to overcome the disadvantages of the prior art. More particularly, it is an object of the invention to provide microcapsules that feature high diffusion density and simultaneously have an easily breakable capsule wall in order thus to assure sufficient release of the encapsulated active.

DESCRIPTION OF THE INVENTION

This object is achieved in full by the invention herein. The invention firstly relates to microcapsules comprising
 (a) a core comprising at least one active, and
 (b) a capsule wall,
wherein the capsule wall consists of at least three polymer layers and at least one of the polymer layers consists of a first phenolic resin, wherein the first phenolic resin comprises 3% to 50% by weight of moieties that derive from at least one aromatic polyol, and at least one further polymer layer consists of a second phenolic resin, wherein the second phenolic resin comprises 3% to 50% by weight of moieties that derive from at least one triphenol.

BRIEF DESCRIPTION OF THE DRAWINGS

The present invention will be described in greater detail with reference to the accompanying drawings, in which FIG. 1 schematically illustrates the structure of the microcapsule in accordance with the present invention.

It has been found that, surprisingly, the microcapsules of the invention are particularly stable to diffusion but nevertheless have a capsule wall that assures release of the active present in the end product even under very low to zero friction, but are nevertheless storage-stable. This is assured in that the capsule wall has at least three polymer layers, wherein one of the three polymer layers consists of a first phenolic resin, wherein the first phenolic resin comprises moieties that derive from at least one aromatic polyol, and at least one further polymer layer consists of a second phenolic resin, wherein the second phenolic resin comprises moieties that derive from at least one triphenol. The inner polymer layer in the context of the invention is the part of the capsule wall that directly adjoins the core of the microcapsule, and hence the active. Adjoining the inner polymer layer is the middle polymer layer, which likewise adjoins the outer polymer layer.

Figure 1:
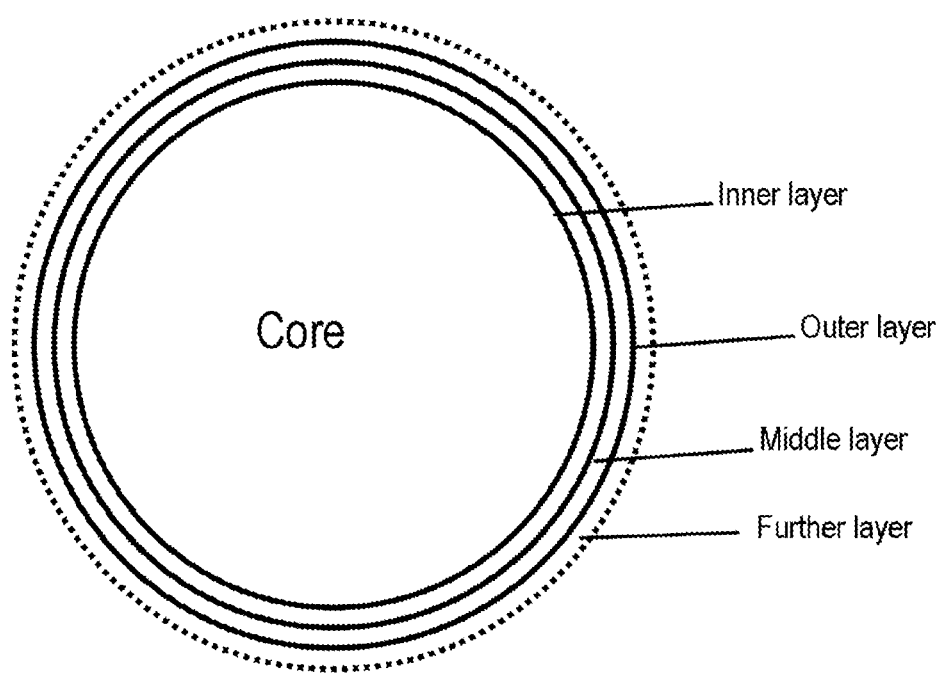
FIG. 1 shows the structure of the microcapsules once again in an illustrative manner. It will be apparent that the capsule wall may also contain further layers, which then in turn adjoin the outer layer shown in FIG. 1.

A further advantage of the at least three polymer layers is that these have a very thin-wall configuration and consequently lead to a generally very thin capsule wall. This of course also affects the amount of polymer to be used, which is reduced as a result by up to 90% compared to a microcapsule having just one polymer layer, especially by 50% to 90%. These thin layers are also advantageous since only a small amount of polymers has to be used as a result. This of course additionally saves material costs. Moreover, the capsules of the present invention allow rapid release of the active, but are nevertheless fully mechanically durable.

A further advantage is that the adhesion properties of the microcapsules are improved, especially the adhesion properties on laundry. This is assured in that the capsule wall is composed of at least three polymer layers, wherein each of the at least three polymer layers is very thin and at least one of the polymer layers consists of a first phenolic resin, wherein the first phenolic resin comprises moieties that derive from at least one aromatic polyol, and at least one further polymer layer consists of a second phenolic resin, wherein the second phenolic resin comprises moieties that derive from at least one triphenol. This structure thus alters the surface charge of the capsule per se, which assures better adhesion to anionic substances, for example cotton.

As already described in the object of the invention, it is accordingly a feature of the microcapsules that they have high diffusion density but simultaneously have an easily breakable capsule wall in order thus to assure sufficient release of the encapsulated active. This is achieved by the addition of at least one aromatic polyol in at least one polymer layer and the addition of at least one triphenol in a further polymer layer. The addition of the polyol and of the triphenol firstly results in a high stability of the microcapsules and secondly in the reduction in the capsule wall per se, which, as mentioned above, saves costs with regard to the amount of polymer to be used and assures release of the active.

The inner layer of the capsule wall preferably consists of a first phenolic resin, wherein the first phenolic resin comprises 3-50% by weight, preferably 5% to 45% by weight, further preferably 10% to 40% by weight, of moieties that derive from an aromatic polyol. In other embodiments of the invention, the first phenolic resin may also comprise 30% to 80%, preferably 40% to 75% by weight, preferably 45% to 65% by weight, of moieties that derive from an aromatic polyol. The middle layer of the capsule wall preferably consists of an amino resin, especially a melamine-formaldehyde resin, wherein the amino resin comprises 3% to 90% by weight, preferably 10% to 85% by weight, preferably 20% to 80% by weight, of moieties that derive from a polyamine, especially melamine. The outer layer of the capsule wall preferably consists of a second phenolic resin, wherein the second phenolic resin comprises 3% to 50% by weight, preferably 5% to 45% by weight, further preferably 10% to 40% by weight, of moieties that derive from a triphenol. In other embodiments of the invention, the second phenolic resin may also comprise 30% to 80%, preferably 40% to 75% by weight, preferably 45% to 65% by weight, of moieties that derive from a triphenol.

In one embodiment of the invention, the at least three polymer layers of the capsule wall each consist of resins comprising moieties that derive from different substances. In a further embodiment of the invention, the at least three polymer layers have an alternating structure, wherein a polymer layer consisting of a phenolic resin is separated in each case by a polymer layer consisting of an amino resin, preferably melamine-formaldehyde resin. In a further embodiment of the invention, the at least three polymer layers have an alternating structure, wherein a polymer layer comprising moieties that derive from the condensation of phenols or polyols with an aldehyde are each separated by a polymer layer comprising moieties that derive from the condensation of polyamines with an aldehyde, especially formaldehyde. In other words, the present invention likewise relates to microcapsules comprising (a) a core comprising at least one active, and (b) a capsule wall, wherein the capsule wall consists of at least three polymer layers and at least one of the polymer layers comprises moieties that derive from the condensation of at least one aromatic polyol and at least one aldehyde, and at least one further polymer comprises moieties that derive from the condensation of at least from triphenol and at least one aldehyde.

Thus, a particularly preferred embodiment of the invention may consist, for example, of a first polymer layer composed of moieties that derive from the condensation of resorcinol and aldehyde, a second polymer layer composed of moieties that derive from the condensation of melamine and aldehyde, and a third polymer layer composed of moieties that derive from the condensation of phloroglucinol and aldehyde. Or a first composed of triethanolamine-formaldehyde moieties, a second composed of resorcinol-aldehyde moieties, and a third composed of phloroglucinol-aldehyde moieties. Or a first composed of melamine-formaldehyde moieties, a second composed of resorcinol-formaldehyde moieties, and a third composed of phloroglucinol-aldehyde moieties. Of course, rather than an amine-formaldehyde component, it is also possible to use precondensates such as Luracoll® SD.

A further particularly preferred embodiment of the invention consists of a first polymer layer consisting of a first phenolic resin, wherein the first phenolic resin comprises moieties that derive from resorcinol, a second polymer layer consisting of amino resin, wherein the amino resin comprises moieties that derive from melamine, and a third polymer layer consisting of a second phenolic resin, wherein the second phenolic resin comprises moieties that derive from phloroglucinol. Or a first composed of triethanolamine-formaldehyde moieties, a second composed of resorcinol moieties, and a third composed of phloroglucinol moieties. Or a first composed of melamine-formaldehyde moieties, a second composed of resorcinol moieties, and a third composed of phloroglucinol moieties. Of course, rather than an amine-formaldehyde component, it is also possible to use precondensates such as Luracoll® SD.

What is meant by "moiety" or "moieties" is a chemical unit which is part of a polymer and is derived from a particular molecule. The above-described polymer layers may be any polymer layers that comprise the above-described moieties. These may be prepared by one of the many suitable methods that are known in the specialist field. In other words, the above-described polymer layers consist of different resins, for example phenolic resins or amino resins, especially melamine-formaldehyde resins, comprising the above-described moieties.

In the context of the invention, all percentages are percentages by weight, unless specifically stated otherwise.

In a particularly preferred embodiment, the aromatic polyol moieties derive from resorcinol.

A triphenol in the context of the invention is a trihydric phenol, i.e. a phenol having three hydroxyl groups. Suitable triphenols are, for example, phloroglucinol (1,3,5-trihydroxybenzene), pyrogallol (1,2,3-trihydroxybenzene) or hydroxyhydroquinone (1,2,4-trihydroxybenzene). Preferred triphenols are 1,3,5-triaminoalkylbenzene and phloroglucinol. In a preferred embodiment of the invention, the outer polymer layer of the capsule wall consists of a second phenolic resin, wherein the second phenolic resin comprises a moiety that derives from at least one triphenol. The particularly preferred triphenol here is phloroglucinol.

In a preferred embodiment of the invention, the capsule wall consists of three polymer layers. In a further-preferred embodiment of the invention, the three polymer layers of the capsule wall each consist of different resins, wherein the resins comprise moieties that derive from different substances. In a preferred embodiment, the outer polymer layer consists of a second phenolic resin, wherein the second phenolic resin comprises moieties that derive from phloroglucinol. In a further preferred embodiment, the middle polymer layer consists of an amino resin, wherein the amino resin comprises moieties that derive from a mixture of melamine and formaldehyde. In a further preferred embodiment, the inner polymer layer consists of a first phenolic resin, wherein the first phenolic resin comprises moieties that derive from resorcinol. The simultaneous use of moieties that derive from resorcinol and phloroglucinol in different polymer layers is additionally particularly advantageous, since this actually enables formation of a three-layer capsule wall that additionally meets all requirements, such as stability, efficient perfume release etc. As already stated further up, particularly thin capsule walls are thus enabled. In a particularly preferred embodiment, the outer polymer layer consists of a second phenolic resin, wherein the second phenolic resin comprises moieties that derive from phloroglucinol, and the middle polymer layer consists of an amino resin, wherein the amino resin comprises moieties that derive from mixtures of melamine and formaldehyde, and the inner polymer layer consists of a first phenolic resin, wherein the first phenolic resin comprises moieties that derive from resorcinol.

In one embodiment of the invention, the inner polymer layer of the microcapsules of the invention is a first phenolic resin, wherein the first phenolic resin comprises moieties that derive from at least one aromatic polyol. In a preferred embodiment, the moieties that the first resin comprises derive from resorcinol.

In one embodiment of the invention, the middle polymer layer of the microcapsules of the invention is an amino resin, especially a melamine-formaldehyde resin, wherein the amino resin comprises moieties that derive from at least one polyamine. In a preferred embodiment, the moieties that the amino resin comprises derive from melamine.

In one embodiment of the invention, the outer polymer layer of the microcapsules of the invention is a second phenolic resin, wherein the second phenolic resin comprises moieties that derive from at least one triphenol. In a preferred embodiment, the moieties that the second phenolic resin comprises derive from phloroglucinol.

Phenolic resins in the context of the invention are synthetic resins (condensation resins) that are produced by polycondensation from phenols and aldehydes. Important starting materials for preparation of the resins are, for example, phenol and formaldehyde. Amino resins in the context of the invention are curable synthetic resins that are prepared by polycondensation of aldehydes and compounds having NH or $NH_2$ groups, for example urea, melamine or dicyandiamide. In a particularly preferred embodiment of the invention, formaldehyde is used as aldehyde.

In a further-preferred embodiment, the capsule wall content based on the slurry is 0.3% to 3% by weight. In a further-preferred embodiment of the invention, the capsule wall content based on the slurry is 0.3% to 2% by weight. In a further-preferred embodiment of the invention, the capsule wall content based on the slurry is 0.3% to 0.9% by weight. Microcapsules of the above-described type are provided in a slurry with a solids content of typically 20% to 50%, preferably 30% to 45%, where the term "solids content" relates to the total weight of microcapsules. The average size of the microcapsules may be between 1 micrometer and 100 micrometers or more. The selection of the most suitable microcapsule size range and of the suitable size distribution depends on the application envisaged.

A "slurry" in the context of the invention is nothing more than a suspension in water.

In a further-preferred embodiment of the invention, the capsule wall content, based on the active, especially on the perfume oil, is 0.5% to 7% by weight. In a further-preferred embodiment of the invention, the capsule wall content, based on the active, especially on the perfume oil, is 0.5% to 5% by weight. In a further-preferred embodiment of the invention, the capsule wall content, based on the active, especially on the perfume oil, is 0.5% to 4% by weight. In a further-preferred embodiment of the invention, the capsule wall content, based on the active, especially on the perfume oil, is 0.7% to 4% by weight. In a further-preferred embodiment of the invention, the capsule wall content, based on the active, especially on the perfume oil, is 0.7% to 3% by weight.

Polyamines/Precondensates

Preferred polyamines in the context of the invention are what are called polyamine precondensates, especially amine-formaldehyde precondensates (AFP). In a preferred embodiment, these constitute the material that ultimately forms the shell or wall of the capsule through polycondensation and encloses the active.

The amine component of the AFP is typically urea or especially melamine. Since the polycondensation, however, is thermally controlled, it is sometimes difficult to control. In general, amino resins are prepared by polycondensation of formaldehyde with compounds containing two or more amino groups (e.g. urea, thiourea, melamine, cyanamide, diaminohexane, benzoguanamine). This reaction proceeds, in a first step, via the addition of urea to form N-hydroxymethyl groups, followed by chain growth via polycondensation with elimination of water. This reaction is usually conducted in basic solution since OH— ions are required as catalyst, and uncrosslinked precondensates are formed. The precondensates are stable at room temperature for several months. The preferred AFPs are therefore alkylation products of melamine with short chain alcohols and especially what are called highly or partly alkoxylated and possibly also alkylated melamines, as supplied in aqueous methanolic formaldehyde solution by BASF under the Luracoll® name, especially Luracoll® SD.

Reaction between melamine and formaldehyde was discovered, for example, by J. Liebig as early as 1834 and has been used industrially since 1936. It can be described by the following scheme:

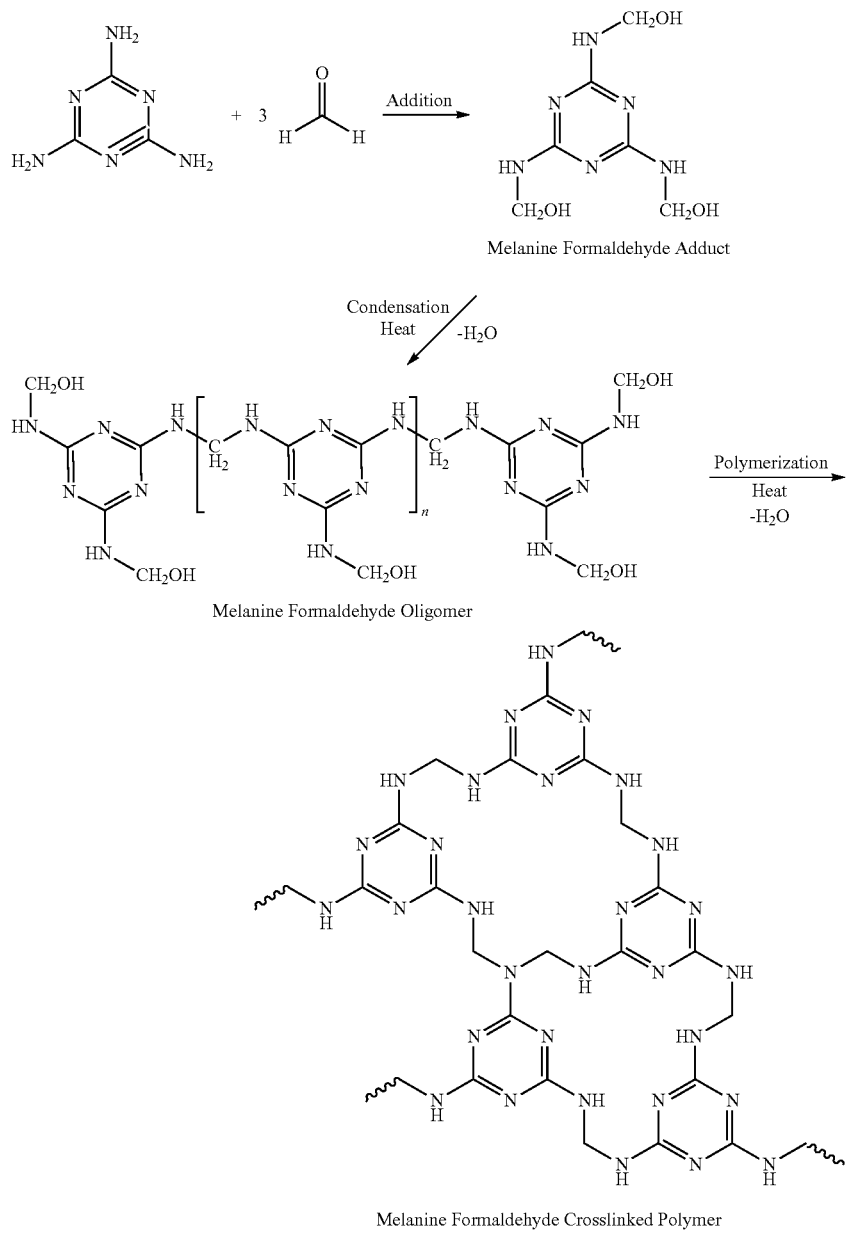

Melanine Formaldehyde Crosslinked Polymer

Useful polyamines preferably include: optionally alkylated mono- and polymethylolurea and mono- and polymethylolmelamine precondensates, as sold, for example, under the URAC name (Cytec Corp.), or else partially methylated mono- and polymethylol-1,3,5-triamino-2,4,6-triazine precondensates, which are commercially available under the CYMEL name (Cytec Corp.). Also useful, finally, are mono- and polyalkylolbenzoguanamine or mono- and polyalkylolglycoluril precondensates. If these precondensates have alkyl groups, they are less reactive and are storable for a longer period. The preferred precondensates comprise the polymethylolmelamines and the polymethylol-1-(3,5-dihydroxymethylbenzyl)-3,5-triamino-2,4,6-triazine.

It is likewise possible to use poly[N-(2,2-dimethoxy-1-hydroxy)]polyamines, for example di[N-(2,2-dimethoxy-1-hydroxy)]urea, tri-[N-(2,2-dimethoxy-1-hydroxy)]melamine, tetra[N-(2,2-dimethoxy-1-hydroxy)]glycoluril and di[N-(2,2-dimethoxy-1-hydroxy)]benzoguanidine and mixtures thereof.

In a particularly preferred embodiment, useful polyamines are melamine-formaldehyde, directly and/or in the form of Luracoll® SD precondensate.

Actives

The selection of raw materials to be encapsulated is uncritical per se and is determined exclusively by the desired application. The only limiting factor is that these must either be in oil form or be sufficiently oil-soluble, i.e. lipophilic, to be soluble in an oil phase, preferably together with the aromatic polyol.

As well as aromas for the foods sector, useful actives are especially perfume oils and oil-soluble odorants as listed hereinafter by way of example:

Extracts from natural raw materials, such as essential oils, concretes, absolutes, resins, resinoids, balsams, tinctures for example ambra tincture; amyris oil; angelica seed oil; angelica root oil; anis oil; valerian oil; basil oil; tree moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill oil; dill seed oil; eau de brouts absolute; oakmoss absolute; elemi oil; estragon oil; *Eucalyptus citriodora* oil; eucalyptus oil; fennel oil; pine needle oil; galbanum oil; galbanum resin; geranium oil; grapefruit oil; guaiac wood oil; gurjun balsam; gurjun balsam oil, helichrysum absolute; helichrysum oil; ginger oil; iris root absolute; iris root oil; jasmine absolute; calamus oil; camellia oil blue; camellia oil roman; carrot seed oil; cascarilla oil; pine needle oil; spearmint oil; cumin oil; labdanum oil; labdanum absolute; labdanum resin; lavandin absolute; lavandin oil; lavender absolute; lavender oil; lemon grass oil; lovage oil; lime oil distilled; lime oil pressed; linalool oil; *Litsea cubeba* oil; laurel leaf oil; macis oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; oregano oil; palmarosa oil; patchouli oil; perilla oil; Peruvian balsam oil; parsley leaf oil; parsley seed oil; petitgrain oil; peppermint oil; pepper oil; allspice oil; pine oil; poley oil; rose absolute; rosewood oil; rose oil; rosemary oil; sage oil dalmatian; sage oil Spanish; sandalwood oil; celery seed oil; spike lavender oil; star anis oil; styrax oil; tagetes oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine yeast oil; vermouth oil; wintergreen oil; ylang oil; ysop oil; civet absolute; cinnamon leaf oil; cinnamon bark oil; and fractions thereof or ingredients isolated therefrom;

individual odorants from one or more of the following groups:

hydrocarbons, for example 3-carene; a-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene;

aliphatic alcohols, for example hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and acetals thereof, for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyloxyacetaldehyde;

aliphatic ketones and oximes thereof, for example 2-heptanone; 2-octanone; 3-octanone; 2-nonanone; 5-methyl-3-heptanone; 5-methyl-3-heptanonoxime; 2,4,4,7-tetramethyl-6-octen-3-one;

aliphatic sulfur-containing compounds, for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

aliphatic nitriles, for example 2-nonenonitrile; 2-tridecenonitrile; 2,12-tri-decenonitrile; 3,7-dimethyl-2,6-octadienonitrile; 3,7-dimethyl-6-octenonitrile;

aliphatic carboxylic acids and esters thereof, for example (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyl oxyacetate; methyl 3,7-dimethyl-2,6-octadienoate;

acyclic terpene alcohols, for example citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, and 3-methyl-2-butenoates thereof;

acyclic terpene aldehydes and ketones, for example geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, and 7-hydroxy-3,7-dimethyloctanal;

cyclic terpene alcohols, for example menthol; isopulegol; a-terpineol; terpinenol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, and 3-methyl-2-butenoates thereof;

cyclic terpene aldehydes and ketones, for example menthone; isomenthone; 8-mercaptomenthan-3-one; carvone; camphor; fenchone; a-ionone; beta-ionone; a-n-methyl ionone; beta-n-methylionone; a-isomethylionone; beta-isomethylionone; a-irone; a-damascone; beta-damascone; beta-damascenone; ?-damascone; d-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8 (5H)-one; nootkatone; dihydronootkatone; a-sinensal; beta-sinensal; acetylated cedar wood oil (methyl cedryl ketone);

cyclic alcohols, for example 4-tert-butylcyclohexanol; 3,3,5-trimethylcyclohexanol; 3-isocamphylcyclohexanol; 2,6,9-trimethyl-(Z2,Z5,E9)-cyclododecatrien-1-ol; 2-isobutyl-4-methyltetrahydro-2H-pyran-4-ol;

from the group of the cycloaliphatic alcohols for example a,3,3-trimethyl-cyclohexylmethanol; 2-methyl-4-(2,2, 3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers, for example cineol; cedryl methyl ether; cyclododecyl methyl ether; (ethoxymethoxy)cyclododecane; a-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic ketones, for example 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 9-cycloheptadecen-1-one; cyclopentadecanone; cyclohexadecanone;

cycloaliphatic aldehydes, for example 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

cycloaliphatic ketones, for example 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octa-hydro-2-naphthalenyl methyl ketone; methyl 2,6,10-trimethyl-2,5,9-cyclododecatrienyl ketone; tert-butyl 2,4-dimethyl-3-cyclohexen-1-yl ketone;

esters of cyclic alcohols, for example 2-tert-butylcyclohexyl acetate; 4-tert-butylcyclo-hexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or -6-indenyl acetate; 4,7-methano-3a,4,5,6,7,7a-hexahydro-5- or -6-indenyl propionate; 4,7-methano-3a,4,5,6,7,7a-hexahydro-5- or -6-indenyl isobutyrate; 4,7-methanooctahydro-5- or -6-indenyl acetate;

esters of cycloaliphatic carboxylic acids, for example allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

aromatic hydrocarbons, for example styrene and diphenylmethane;

araliphatic alcohols, for example benzyl alcohol; 1-phenethyl alcohol; 2-phenethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, for example benzyl acetate; benzyl propionate; benzyl isobutyrate; benzyl isovalerate; 2-phenethyl acetate; 2-phenethyl propionate; 2-phenethyl isobutyrate; 2-phenethyl isovalerate; 1-phenethyl acetate; a-trichloromethylbenzyl acetate; a,a-dimethylphenethyl acetate; a,a-dimethyl-phenethyl butyrate; cinnamyl acetate; 2-phenoxyethyl isobutyrate; 4-methoxybenzyl acetate;

araliphatic ethers, for example 2-phenethyl methyl ether; 2-phenethyl isoamyl ether; 2-phenethyl 1-ethoxyethyl ether; phenylacetaldehyde dimethyl acetal; phenylacetaldehyde diethyl acetal; hydratropic aldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, for example benzaldehyde; phenylacetaldehyde; 3-phenylpropanal; hydratropic aldehyde; 4-methylbenzaldehyde; 4-methylphenyl-acetaldehyde; 3-(4-ethylphenyl)-2,2-dimethylpropanal; 2-methyl-3-(4-isopropylphenyl)-propanal; 2-methyl-3-(4-tert-butylphenyl)propanal; 3-(4-tert-butylphenyl)propanal; cinnamaldehyde; a-butylcinnamaldehyde; a-amylcinnamaldehyde; a-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones, for example acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and esters thereof, for example benzoic acid; phenylacetic acid; methyl benzoate; ethyl benzoate; hexyl benzoate; benzyl benzoate; methylphenyl acetate; ethylphenyl acetate; geranylphenyl acetate; phenethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

nitrogen-containing aromatic compounds, for example 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenonitrile; 5-phenyl-3-methylpentanonitrile; methyl anthranilate; methyl N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexene-carbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine; 4-(4,8-dimethyl-3,7-nonadienyl)pyridine;

phenols, phenyl ethers and phenyl esters, for example estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate;

from the group of the heterocyclic compounds, for example 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, for example 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecandioate; ethylene-1,13-tridecandioate; coumarin; 2,3-dihydrocoumarin; octahydrocoumarin.

Stabilizers and Protective Colloids

The emulsions preferably also additionally comprise stabilizers or protective colloids. Suitable examples include, in particular, acrylic copolymers that have sulfonate groups, for example LUPASOL® PA140 or LUPASOL® VFR (BASF). Likewise suitable are copolymers of acrylamides and acrylic acid, copolymers of alkyl acrylates and N-vinylpyrrolidone, for example LUVISKOL® K15, K30 or K90 (BASF); sodium polycarboxylates, sodium polystyrenesulfonates, vinyl ether- and methyl vinyl ether-maleic anhydride copolymers, and ethylene-, isobutylene- or styrene-maleic anhydride copolymers.

The preferred stabilizers are the abovementioned representatives from the LUPASOL® series, especially in combination with AFP of the LURACOLL® type.

The use amount of the stabilizers may be in the range from about 1% to about 10% by weight and especially about 2% to about 5% by weight—based on the emulsion.

Use of stabilizers during the production of the microcapsules of the invention may be advantageous since this additionally reduces possible color changes.

Production Method

The present invention also provides a method of producing the above-described microcapsules, comprising the following steps:

(a) providing a first aqueous formulation comprising at least one aldehyde or at least one polyamine precondensate;
(b) providing an oil phase comprising the active to be encapsulated and at least one aromatic polyol;
(c) mixing the aqueous phase with the oil phase in the presence of at least one emulsifier and/or stabilizer to form an emulsion;
(d) initiating the polymerization;
(e) adding at least one polyamine or a polyamine precondensate;
(f) leaving the mixture to rest at 40 to 70° C. for 40 to 80 minutes;
(g) adding at least one triphenol;
(h) adding at least one aldehyde or at least one polyamine precondensate;
(i) leaving the mixture to rest at 40 to 70° C. for 40 to 80 minutes;
(j) crosslinking and curing the microcapsules obtained, and optionally
(k) separating the microcapsules from the dispersion and drying.

What is important here is that the aromatic polyol from step (b) is added to the oil phase. This has the advantage that higher storage stabilities can be achieved in spite of a thinner capsule wall overall.

In a preferred embodiment of the invention, the mixture is left at rest in step (f) at 50 to 65° C. for 50 to 70 minutes. In a very preferred embodiment, the mixture is left at rest in step (f) at about 60° C. for about 60 minutes.

In a preferred embodiment of the invention, the mixture is left at rest in step (i) at 50 to 65° C. for 50 to 70 minutes. In a very preferred embodiment, the mixture is left at rest in step (f) at about 60° C. for about 60 minutes.

In one embodiment of the invention, after step (c), blanketing of the reaction with $CO_2$ additionally takes place. This blanketing with $CO_2$ has the advantage that discoloration caused by aromatic polyols in the core are reduced.

Any of the above-enumerated polyamines (step (e)) or precondensates (steps (a) and (e)) may be used in the method of the invention. In a preferred embodiment of the invention, polyamine precondensates selected from the group formed by optionally alkylated mono- and polymethylolurea or mono- and polymethylolmelamine precondensates, partially methylated mono- and polymethylol-1,3,5-triamino-2,4,6-triazine precondensates, mono- and polyalkylolbenzoguanamine precondensates and mono- and polyalkylolglycoluril precondensates, poly[N-(2,2-dimethoxy-1-hydroxy)] polyamines, melamine-formaldehyde, Luracoll SD and mixtures thereof are used.

In a particularly preferred embodiment, the aldehyde used in step (a) is formaldehyde. In a further particularly preferred embodiment, the polyamine/precondensate used in step (e) is Luracoll SD.

Any of the above-enumerated actives may be used in the production method of the invention. In a preferred embodiment of the invention, the active to be encapsulated is a perfume oil.

In one embodiment of the invention, directly after step (i), the mixture is heated to 80° C. to 90° C. This step serves to form the outer polymer layer of the capsule wall. In a particularly preferred embodiment, the triphenol is phloroglucinol.

In a further embodiment of the invention, on initiation of the polymerization in step (d), the pH is lowered to a value of 3 to 5 by the addition of formic acid or a mixture of formic acid, citric acid and ascorbic acid. This lowering of the pH in turn serves to prevent unwanted color reactions of the aromatic polyol. Color reactions are of course undesirable, particularly with regard to the use of the microcapsules, for example in fabric softeners, and must be avoided as far as possible. This is possible by virtue of the described lowering of the pH on initiation of the polymerization of the first polymer layer.

In a further embodiment of the invention, the addition of at least one aromatic polyol in step (b) and the addition of at least one triphenol in step (g) enables the formation of at least three polymer layers, and likewise the formation of a capsule wall that is very thin overall. This is possible even though the capsule wall in the context of the invention consists of at least three polymer layers. Compared to microcapsules consisting of 1 or 2 layers, thinner capsule walls are formed, which on the one hand saves material costs but at the same time assures better stability. In a preferred embodiment of the invention, the aromatic polyol is resorcinol and the triphenol is phloroglucinol.

Crosslinking or curing of the capsules can be accomplished using any of the substances described in the prior art. Examples of crosslinkers in the context of the invention are valeraldehyde, capronaldehyde, caprylaldehyde, decanal, succinaldehyde, cyclohexanecarbaldehyde, cyclopentanecarbaldehyde, 2-methyl-1-propanal, 2-methylpropionaldehyde, acetaldehyde, acrolein, aldosterone, antimycin A, 8-apo-β-caroten-8-al, benzaldehyde, gutanal, chloral, citral, citronellal, crotonaldehyde, dimethylaminobenzaldehyde, folic acid, fosmidomycin, furfural, glutaraldehyde, glyceraldehyde, glycolaldehyde, glyoxal, glyoxylic acid, heptanal, 2-hydroxybenzaldehyde, 3-hydroxybutanal, hydroxymethylfurfural, 4-hydroxynonenal, isobutanal, isobutyraldehyde, methacrolein, 2-methylundecanal, mucochloric acid, N-methylformamide, 2-nitrobenzaldehyde, nonanal, octanal, oleocanthal, orlistat, pentanal, phenylethanal, phycocyanin, piperonal, propanal, propenal, protocatechualdehyde, retinal, salicylaldehyde, secologanin, streptomycin, strophanthidin, tylosin, vanillin, cinnamaldehyde, dimethoxyethanal.

Further useful crosslinkers include an aromatic alcohol from the phenols having two or more hydroxyl groups, preferably from pyrocatechol, resorcinol, hydroquinone and 1,4-naphthohydroquinone, phloroglucinol, pyrogallol, hydroxyhydroquinone, cresols & phenols, methoxyphenols, naphthols, thymol, ethyl- or propylphenols, 1,3,5-triaminobenzene, 1,3,5-triaminoalkylbenzene, 1,3,5-trialkoxyaminobenzene, 1,3,5-triamidobenzene.

Further useful crosslinkers include heterocyclic compounds having at least one nitrogen atom as heteroatom, which is adjacent either to an amino-substituted carbon atom or to a carbonyl group, for example pyridazine, pyrimidine, pyrazine, pyrrolidone, aminopyridine and compounds derived therefrom, aminopyridines, for example melamine, 2,6-diaminopyridine, substituted and dimeric aminopyridines and mixtures prepared from these compounds, polyamides and dicyandiamide, urea and derivatives thereof, and pyrrolidone and compounds derived therefrom, for example imidazolidinone, hydantoin and derivatives thereof, allantoin and derivatives thereof, triamino-1,3,5-triazine (melamine).

It will be apparent that all crosslinkers may be combined with one another.

Any of the other substances or constituents mentioned above may of course also be part of the preparation method and are not enumerated separately once again.

INDUSTRIAL APPLICABILITY

The present invention further relates to cosmetic formulations, pharmaceutical products, domestic and cleaning products and industrial compositions, for example adhesive and coating compositions, paints, varnishes, binders, materials such as plastics, paper, textiles, lubricants, building materials, dyes, organic and inorganic powders, pigment dispersions, agrochemicals, phase transition materials, flame retardants containing the microcapsules of the invention.

In a preferred embodiment of the invention, the microcapsules are used in washing and cleaning products, cosmetic formulations or perfume compositions.

EXAMPLES

Production Method
The production of a capsule of the invention is described hereinafter. This features the following steps:
Forming the First Polymer Layer:
1. Dissolving the aromatic polyol, preferably resorcinol, in the oil phase of the fragrance, adding formaldehyde to the aqueous phase.
2. Initiating the polymerization by acidifying to pH 3-5 with formic acid or a mixture of formic acid, citric acid and ascorbic acid to block color reactions.
3. Heating to 60° C. to 70° C.
4. Optionally blanketing the reaction with CO2.
Forming the Second Polymer Layer:
5. Adding the polyamine, preferably melamine-formaldehyde or Luracoll SD dissolved in water.
6. Dissolving the Lupasol PA140 protective colloid in water.
7. Leaving the mixture to rest at 60° C. for 60 min.
8. Optionally acidifying in order to adjust the pH.
Forming the Third Polymer Layer:
9. Adding at least one triphenol, preferably phloroglucinol.
10. Adding formaldehyde or Luracoll SD.
11. Leaving the mixture to rest at 60° C. for 60 min.
12. Optionally heating to 80° C.-90° C.
13. Subsequently cooling to 35° C.
14. Optionally adding further substances for further hardening of the capsules.

Illustrative compositions of the microcapsules of the invention are given in Table 1 below:

TABLE 1

| Sample | Water [g] | Perfume [g] | Resorcinol [g] | Lupasol [g] | Luracoll [g] | Phloroglucinol [g] |
| --- | --- | --- | --- | --- | --- | --- |
| 1 | 90 | 180 | 3 | 8 | 3.68 | 5 |
| 2 | 120 | 180 | 2.5 | 8 | 5.43 | 5 |
| 3 | 90 | 180 | 2 | 15 | 3.68 | 2 |
| 4 | 90 | 180 | 1 | 8 | 3.68 | 0.9 |
| 5 | 120 | 180 | 0.7 | 15.75 | 3.65 | 0.9 |
| 6 | 120 | 180 | 0.49 | 11.03 | 2.56 | 0.63 |
| 7 | 120 | 180 | 0.35 | 15.75 | 1.83 | 0.45 |
| 8 | 80 | 180 | 0.2 | 5.51 | 1.28 | 0.33 |

Further Illustrative Production Methods:

15 g of Lupasol PA140 and 2.5 g of formalin, 37%, are dissolved in 120 g of demineralized water, a solution of 180 g of perfume and 1.05 g of resorcinol is added at 35° C. while stirring, and the pH is adjusted to 3.5 with about 2 g of formic acid, 10%. This is followed by stirring at 35° C. for 30 min. The temperature is then heated to 60° C. over a period of 30 min. 1.7 g of melamine and 2.5 g of formalin, 37%, are added and the mixture is stirred at 60° C. for a further 30 min. Lastly, 1.5 g of phloroglucinol and 2.5 g of formalin, 37%, are added and the mixture is stirred at 60° C. for a further 3 h.

50 g of formalin, 37%, is dissolved in 60 g of demineralized water. 12.3 g of melamine is dispersed, the pH is adjusted to 8.0 with about 1 g of triethanolamine, and the mixture is stirred at 70° C. until the solution becomes slightly opaque again (about 90 min). 60 g of cold demineralized water is added. A solution of 180 g of perfume and 1.05 g of resorcinol is added and emulsified while stirring. About 30 g of citric acid, 25%, is used to establish a pH of 4.5, and the temperature is adjusted to 40° C. The mixture is stirred at 40° C. for a further 1 h. This is followed by heating to 60° C. and stirring for a further 1 h. Lastly, 1.5 g of phloroglucinol is added and the mixture is stirred at 60° C. for a further 3 h.

30 g of formalin, 37%, 9 g of urea and about 1 g of triethanolamine are dissolved in 60 g of demineralized water. The pH is adjusted to 8.0 and the mixture is stirred at 70° C. until the solution becomes slightly opaque again (about 2 h). 60 g of cold demineralized water is added. A solution of 180 g of perfume and 1.05 g of resorcinol is added and emulsified while stirring. About 30 g of citric acid, 25%, is used to establish a pH of 4.0, and the temperature is adjusted to 40° C. The mixture is stirred at 40° C. for a further 1 h. This is followed by heating to 60° C. and stirring for further 1 h. Lastly, 1.5 g phloroglucinol is added and the mixture is stirred at 60° C. for a further 3 h.

15 g of Lupasol PA140 and 2.5 g of paraformaldehyde are dissolved in 120 g of demineralized water, a solution of 180 g of perfume and 1.05 g of resorcinol is added at 35° C. while stirring, and about 2 g of 10% formic acid is used to adjust the pH to 3.5. This is followed by stirring at 35° C. for a further 30 minutes. Then the mixture is heated up 60° C. within 30 minutes. 7.5 g of Luwipal63 is added and the pH is readjusted to 3.5. Subsequently, 1.5 g phloroglucinol and 2.5 g of paraformaldehyde are added, and the mixture is stirred at 60° C. for a further 1 hour. Subsequently, the temperature is increased to 80° C. and the mixture is stirred once again for 2 hours.

The capsules of the invention were compared with prior art capsules (1 polymer layer and 2 polymer layers) with regard to their stability and adhesion properties. The comparison was made as follows: the samples were diluted in a ratio of 1:10 with demineralized water and then placed into a measurement cell. The test method was adjusted depending on the respective capsule sizes (Smoluchowski: capsules/particles >100 nm; Hückel: particles <100 nm). Thereafter, the temperature was adjusted to 25° C. and 3 measurement cycles of 10 measurements were effected. Finally, the average was formed from the values.

The results are shown in table 2:

TABLE 2

Comparison of microcapsules in terms of zeta potential

| capsule type | Zeta potential [mV] | St dev [mV] |
|---|---|---|
| 1 layer/melamine-formaldehyde | −54.2 | 4.5 |
| 2 layers (resorcinol/melamine-formaldehyde) | −52.1 | 6.9 |
| 3 layers (resorcinol/melamine-formaldehyde/phloroglucinol) | −39.2 | 4.5 |

Table 2 shows clearly that a capsule of the invention consisting of three polymer layers has a more positive zeta potential than the prior art capsules. "Zeta potential" generally means the electrostatic potential generated by electrically charged objects in solution. A detailed explanation of the theoretical basis and practical relevance of zeta potential can be found, for example, in "Zeta Potential in Colloid Sciences" (Robert. J. Hunter; Academic Press, London 1981, 1988). Its value constitutes a suitable measure of the ability of the object to establish electrostatic interactions with other objects present in the solution, such as surfactants, polyelectrolytes and surfaces.

Table 2 thus shows clearly that a 3-layer structure of the capsule wall thus reduces surface tension of the capsule, which results in distinctly better adhesion, for example on cotton material.

Table 3 illustrates the correlation between the thickness of the capsule wall and the number of different polymer layers and diffusion stability. It is very clearly shown here that the microcapsules of the invention are much more stable over time with respect to diffusion. This is attributable firstly, as already stated above, to the at least three-layer capsule wall of the invention. The capsules consisting of 1 layer and of 2 layers here are prior art capsules. The capsules consisting of 3 layers are capsules of the invention. All capsules in table 3 have the composition according to table 2. Measurements were made over the course of 12 weeks as to how much residual perfume oil (as a percentage) still remains in the capsule. The more stable the capsule, the more perfume oil must be present in the capsule. The capsules were stored here at 45° C. in fabric softener. The prior art capsules and also the capsules of the invention were also reduced ever further in terms of their shell (wall content [%]). It is thus clearly apparent that the capsules of the invention containing both resorcinol and phloroglucinol, in spite of a thinner shell or capsule wall, have a distinct improvement in stability over a long period of time.

TABLE 3

Stability [%] at 45° C. in fabric softener

| Layers | Wall content [%] based on slurry | Wall content [%] based on perfume oil | 1 week [%] | 4 weeks [%] | 8 weeks [%] | 12 weeks [%] | Free oil based on slurry | Number of capsules destroyed |
|---|---|---|---|---|---|---|---|---|
| 1 | 6.56 | 13.84 | 97 | 86 | 41 | 5 | 0.01% | 0.0% |
| 1 | 1.98 | 4.74 | 93 | 64 | 38 | — | 0.70% | 2.1% |
| 1 | 1.48 | 3.56 | 62 | 26 | — | — | 6.75% | 20.5% |
| 2 | 1.81 | 4.53 | 90 | 67 | 38 | 23 | 0.07% | 0.2% |
| 2 | 1.45 | 3.62 | 82 | 25 | — | — | 8.23% | 20.6% |
| 3 | 2.26 | 5.64 | 94 | 91 | 85 | 72 | 0.02% | 0.1% |
| 3 | 1.78 | 4.45 | 94 | 91 | 82 | 67 | 0.03% | 0.1% |
| 3 | 1.39 | 3.46 | 94 | 91 | 81 | 60 | 0.02% | 0.0% |
| 3 | 0.92 | 2.22 | 79 | 69 | 48 | 32 | 0.09% | 0.2% |

Table 4 shows a comparison of fragrance intensity on cotton material after treatment with a fabric softener. The results reflect the function of the various prior art capsules and the capsules of the invention, before and after rubbing. The different cotton cloths were tested by 40 trained panelists. A scale of 1-9 was employed, with 1 corresponding to no fragrance and 9 to a very strong fragrance. Table 5 likewise illustrates this comparison, but after storage of the capsules at 40° C. for 4 weeks. Here too, it can clearly be seen that the microcapsules of the invention have the highest fragrance intensity, both before and after rubbing. This illustrates that the microcapsules of the invention have high diffusion density, but simultaneously a readily breakable capsule wall, in order thus to assure sufficient release of the encapsulated active. This makes it clear that the use of free unencapsulated perfume oil is unnecessary. Nevertheless, the capsules of the invention are stable enough to ensure that not all the fragrance is released. Storage stability at elevated temperature is also assured by the capsules of the invention.

TABLE 4

Sensory properties of cotton cloths after treatment with fabric softener, 40 panelists, fresh

|  | Before rubbing | After rubbing |
| --- | --- | --- |
| No capsules | 1.5 | 1.3 |
| 1-layer | 2.2 | 4.4 |
| 2-layer | 2.8 | 4.3 |
| 3-layer | 3.9 | 4.7 |

TABLE 5

Sensory properties after 4 weeks at 40° C.

|  | Before rubbing | After rubbing |
| --- | --- | --- |
| No capsules | 1.4 | 1.3 |
| 1-layer | 2.1 | 4.2 |
| 2-layer | 1.4 | 3.7 |
| 3-layer | 3.1 | 4.6 |

Figure 2:
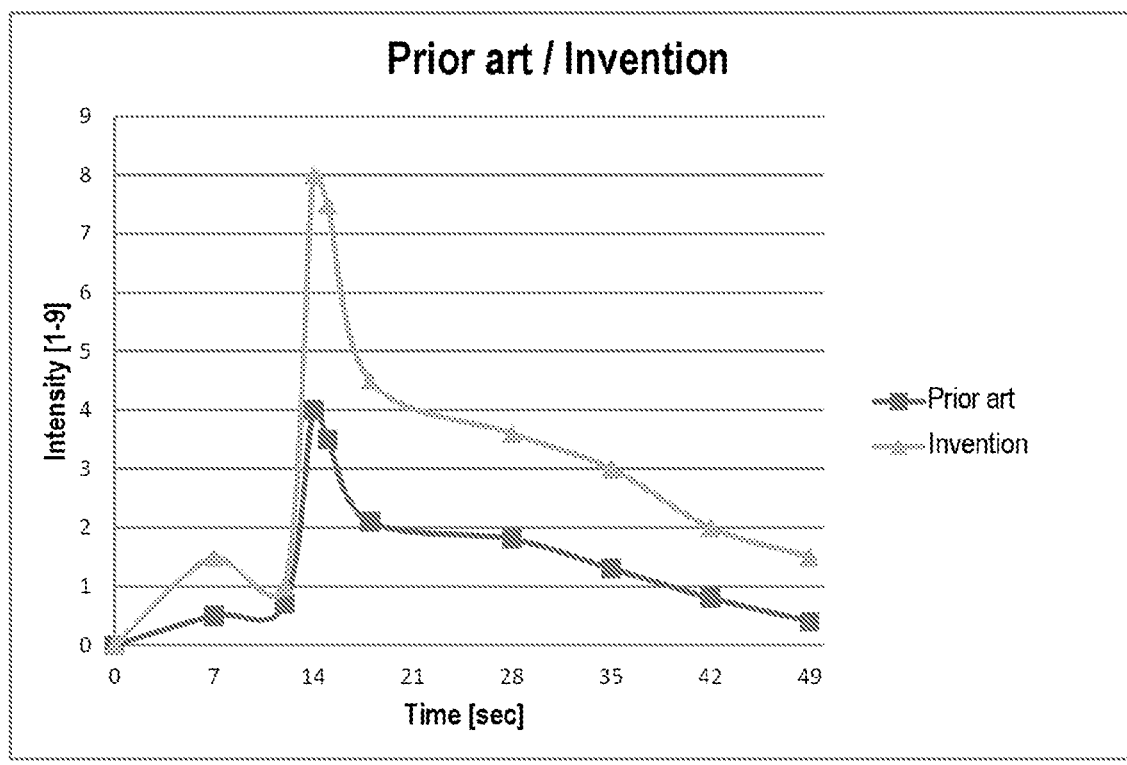
FIG. 2 is a graph documenting improvement of the microcapsule according to the present invention against the prior art.

In addition, 0.2% (w/w) of the microcapsule slurry of the invention and prior art microcapsule slurry was diluted in a commercial fabric softener base and stored at 40° C. for 4 weeks. Subsequently, various material cloths (2 kg) were washed in a European washing machine with 30 g of the fabric softener (once with prior art capsules, once with capsules of the invention) using the "Express 20" program at 900 rpm. The samples were dried overnight and assessed before and after rubbing by a panel of experts (12-15 panelists). The panel of experts assessed the intensity of the samples on the scale of 1-9 (1=odorless; 9=very strong odor) in a different sequence. Each sample was evaluated twice (in duplicate, blind), and the values were averaged. Table 6 and FIG. 2 illustrate the results.

TABLE 6

Sensory properties after 4 weeks at 40° C.

| Time [sec] | Sensory intensity [1-9] | |
| --- | --- | --- |
|  | Prior art | Invention |
| 0 | 0 | 0 |
| 7 | 0.5 | 1.5 |
| 12 | 0.7 | 1 |
| 14 | 4 | 8 |

TABLE 6-continued

Sensory properties after 4 weeks at 40° C.

| Time [sec] | Sensory intensity [1-9] | |
| --- | --- | --- |
|  | Prior art | Invention |
| 15 | 3.5 | 7.5 |
| 18 | 2.1 | 4.5 |
| 28 | 1.8 | 3.6 |
| 35 | 1.3 | 3 |
| 42 | 0.8 | 2 |
| 49 | 0.4 | 1.5 |

Table 6 and FIG. 2 clearly show an improvement over the prior art in terms of the sensory properties of the microcapsules. These results suggest that the capsules are very storage-stable on account of the at least three polymer layers, but enable release of the encapsulated active, especially a perfume oil, through minor mechanical stress, for example rubbing.

The invention claimed is:

1. A microcapsule comprising
   (a) a core comprising at least one active ingredient, and
   (b) a capsule wall,
   wherein the capsule wall comprises at least three polymer layers and at least one of the polymer layers comprises a first phenolic resin,
   the first phenolic resin comprises 3% to 50% by weight of moieties that derive from at least one aromatic polyol, and at least one further polymer layer consists of a second phenolic resin, and
   the second phenolic resin comprises 3% to 50% by weight of moieties that derive from at least one triphenol, and
   wherein the at least three polymer layers have an alternating structure, and a polymer layer comprising a phenolic resin is separated in each case by a polymer layer comprising an amino resin.

2. The microcapsule as claimed in claim 1, wherein the aromatic polyol moieties derive from resorcinol.

3. The microcapsule as claimed in claim 1, wherein the triphenol moieties derive from phloroglucinol.

4. The microcapsule as claimed in claim 1, wherein the capsule wall content, based on the slurry, is 0.3% to 3% by weight.

5. A method of producing the microcapsule as claimed in claim 1, comprising the following steps:
   (a) providing a first aqueous formulation comprising at least one aldehyde or at least one polyamine precondensate;
   (b) providing an oil phase comprising the active to be encapsulated and at least one aromatic polyol;
   (c) mixing the aqueous phase with the oil phase in the presence of at least one emulsifier and/or stabilizer to form an emulsion;
   (d) initiating the polymerization;
   (e) adding at least one polyamine or a polyamine precondensate;
   (f) leaving the mixture to rest at 40 to 70° C. for 40 to 80 minutes;
   (g) adding at least one triphenol;
   (h) adding at least one aldehyde or at least one polyamine precondensate;
   (i) leaving the mixture to rest at 40 to 70° C. for 40 to 80 minutes;
   (j) crosslinking and curing the microcapsules obtained in step (f); and optionally (k) separating the microcapsule from the dispersion and drying.

6. The method as claimed in claim 5, wherein step (c) is followed by blanketing of the reaction with CO2.

7. The method as claimed in claim 6, wherein the blanketing of the reaction with CO2 at least reduces the discoloration of the microcapsule caused by aromatic polyols.

8. The method as claimed in claim 5, wherein the aldehyde and/or precondensate is selected from the group consisting of aldehydes and/or precondensates formed by optionally alkylated mono- and polymethylolurea or mono- and polymethylolmelamine precondensates, partially methylated mono- and polymethylol-1,3,5-triamino-2,4,6-triazine precondensates, mono- and polyalkylolbenzoguanamine precondensates and mono- and polyalkylolglycoluril precondensates, dialdehydes, formaldehyde, and mixtures thereof.

9. The method as claimed in claim 5, wherein the active ingredient to be encapsulated is a perfume oil.

10. The method as claimed in claim 5, wherein, directly after step (i), the mixture is heated to 80° C. to 90° C. to form the outer polymer layer.

11. The method as claimed in claim 5, wherein the triphenol added is phloroglucinol.

12. The method as claimed in claim 5, wherein the polymerization is initiated in step (d) by lowering the pH to a value of 3 to 5 by the addition of formic acid or a mixture of formic acid, citric acid and ascorbic acid to block any color reaction of the aromatic polyol.

13. The method as claimed in claim 6, wherein the addition of at least one aromatic polyol in step (b) and the addition of at least one triphenol in step (f) enables the formation of thin capsule walls.

14. A washing or cleaning composition, cosmetic formulation or perfume composition comprising the microcapsule microcapsules as claimed in claim 1.

15. The microcapsule as claimed in claim 1, wherein the first phenolic resin comprises 5% to 45% by weight of moieties that derive from the at least one aromatic polyol.

16. The microcapsule as claimed in claim 1, wherein the first phenolic resin comprises 10% to 40% by weight of moieties that derive from the at least one aromatic polyol.

17. The microcapsule as claimed in claim 1, wherein the second phenolic resin comprises 5% to 45% by weight of moieties that derive from the at least one triphenol.

18. The microcapsule as claimed in claim 1, wherein the second phenolic resin comprises 10% to 40% by weight of moieties that derive from the at least one triphenol.

19. The microcapsule as claimed in claim 1, wherein the amino resin derives from a polyamine.

20. The microcapsule as claimed in claim 1, wherein the amino resin derives from a melamine.

\* \* \* \* \*